United States Patent
Ackermann et al.

(10) Patent No.: US 6,912,053 B1
(45) Date of Patent: Jun. 28, 2005

(54) RING LASER SCATTEROMETER

(75) Inventors: Mark Ackermann, Albuquerque, NM (US); Jean-Claude Diels, Albuquerque, NM (US)

(73) Assignee: Sandia Corporation, Albuquerque, NM (US)

(*) Notice: Subject to any disclaimer, the term of this patent is extended or adjusted under 35 U.S.C. 154(b) by 246 days.

(21) Appl. No.: 10/390,508

(22) Filed: Mar. 17, 2003

(51) Int. Cl.$^7$ .............................. G01B 9/02; H01S 3/083
(52) U.S. Cl. ............................................ 356/484; 372/94
(58) Field of Search ............................ 356/484; 372/94

(56) References Cited

U.S. PATENT DOCUMENTS

| | | | |
|---|---|---|---|
| 5,251,230 A | | 10/1993 | Lai et al. |
| 5,331,403 A | * | 7/1994 | Rosker et al. ............... 372/94 |
| 5,363,192 A | | 11/1994 | Diels et al. |
| 5,367,528 A | * | 11/1994 | Diels et al. .................. 372/94 |
| 6,441,907 B1 | * | 8/2002 | Son et al. ................... 356/484 |
| 6,650,682 B1 | * | 11/2003 | Diels et al. .................. 372/94 |
| 2003/0189711 A1 | * | 10/2003 | Orr et al. .................... 356/484 |

OTHER PUBLICATIONS

"Ultrashort Laser Pulse Phenomena"; Diels, et al, ppgs. 497–501.

* cited by examiner

Primary Examiner—Gregory J. Toatley, Jr.
Assistant Examiner—Patrick Connolly
(74) Attorney, Agent, or Firm—George H. Libman

(57) ABSTRACT

A scatterometer utilizes the dead zone resulting from lockup caused by scatter from a sample located in the optical path of a ring laser at a location where counter-rotating pulses cross. The frequency of one pulse relative to the other is varied across the lockup dead zone.

15 Claims, 2 Drawing Sheets

RING LASER SCATTEROMETER

The United States Government has rights in this invention pursuant to Department of Energy Contract No. DF-AC04-94AL85000 with Sandia Corporation.

CROSS REFERENCE TO RELATED APPLICATIONS (Not Applicable)

BACKGROUND OF THE INVENTION

Surface roughness is detrimental to precision optical applications. For a theoretical perfect reflective surface, incident light is reflected along a precise angle of reflection. For an actual imperfect reflective surface, the reflected light is scattered in directions other than the angle of reflection.

Scattered light is defined by its magnitude and angular distribution. Optical scatter is characterized through the bidirectional reflection distribution function or BRDF, a function of the ratio of scatter per unit solid angle to the incident power. Machines known as scatterometers, goniometers and gonio-reflectometers are frequently used to map out the hemispheric reflection for determination of BDRF. Present BRDF measurement systems are reasonably sensitive, but that precision suffers at the low end of the measurement range. These measurement systems provide precise and reliable BRDF measurement of surfaces like diffuse white paint, but their measurements get noisy for low scatter materials such as precision mirrors. Current BRDF measurement technologies have difficulty with extremely low scatter samples. While most of the optical energy is reflected in the specular direction, a small amount of energy is scattered elsewhere within the hemisphere above the surface, which contributes to stray light, degrades sensor performance, raises the noise floor and increases with contamination. The measurement of extremely low-scatter optics is complicated and noise limited to about $10^{-6}$/sr.

Scatterometers are optical devices used for surface measurements in quality control applications. A typical scatterometer focuses a collimated (laser) beam of light on a surface, and BDRF is determined by measuring the intensity of the reflected light at different angles with one or more fixed or movable detectors.

This invention utilizes a femtosecond (fs) ring laser with counter-rotating short pulses, as discussed hereinafter. Such pulses have a pulse length on the order of micrometers and consist of only a few cycles of visible light. The details of such a ring laser are known in the art and are discussed, for example, in J. Diels et al., *Ultrashort Laser Pulse Phenomena*, Academic Press, 1996, Chap. 12.2. The ring laser has a laser cavity formed in a continuous path that supports counter-rotating beams. When the ring laser undergoes rotation, one beam experiences a positive Doppler shift and the other beam a negative Doppler shift. Very small differences $\Delta\phi$ in the phase velocity between the two counter-circulating beams result in a frequency difference $\Delta f = \Delta\phi/\tau_{RT}$ which can be measured as a beat note between the two output beams. An example of such detection is shown in U.S. Pat. No. 5,251,230 of one of the inventors. Where the two beams interfere, the frequency difference between the beams is detectable as a beat signal. However, at low rotation rates (such as caused by the rotation of the earth), the frequency of the two beams becomes almost identical, and the beams may lock-up because of light scatter from optical surfaces within the cavity. A 'dead zone' occurs while the beams are locked, as the beat signal is zero.

It is known that lock-up occurs only when the counter-rotating beams overlap. Using ultra-short pulses in a ring laser gyro minimizes lock-up, as such pulses overlap at only a couple of locations within the cavity. According to J. Diels' U.S. Pat. Nos. 5,363,192 and 5,367,528, the pulses should overlap in a region of minimal scattering to avoid lock-up.

As shown in the '230 patent, the phase difference between the two beams can be controlled by a device that varies the index of refraction driven at the cavity round-trip frequency $1/\tau_{RT}$. In the absence of lock-up between the counter-circulating pulses, the beat note is:

$$\Delta f_{ba} = \frac{\Delta n * d}{\lambda * \tau_{RT}} = \frac{f \Delta P}{P} \qquad \text{eq. 1}$$

where $\Delta n$ is the amplitude of the change of index induced by the modulator of thickness d submitted to the voltage $V = V_0 \cos(2\pi\mu/\tau_{RT})$, and $\rho$ is the optical path length.

Either a moving saturable absorber or a synchronously pumped optical parametric oscillator may be used to fix the crossing point for the intracavity pulse envelopes, and at the same time minimize phase coupling. The absorber is discussed in the aforementioned book, *Ultrashort Laser Pulse Phenomena*, Chaps. 5 and 12, while the parametric oscillator is discussed in A. Siegman, *Lasers*, University Science Books, 1986, Chap. 29. The absorber is also discussed in the '528 and '192 patents referenced above.

SUMMARY OF THE INVENTION

It is an object of this invention to use a scatterometer utilizing properties of a pulse ring laser to make measurements of light scatter from a precision mirror.

To achieve the foregoing and other objects, and in accordance with the purpose of the present invention, as embodied and broadly described herein, the invention is a scatterometer comprising a pulsed ring laser having a source for generating counter-rotating pulses within a continuous optical path, the pulses having a pulse length much less than the length of the optical path, and the frequency of said pulses being slightly different. A beat note representative of the frequency difference between the pulses is detected. A sample located in the optical path at a location where the counter-rotating pulses cross creates backscatter that is a function of the beat note detected by the detector.

The invention also is a method of measuring backscattering from an optical sample using counter-rotating pulses along a continuous optical path of a ring laser. A sample is placed in the optical path at a location where the counter-rotating pulses cross, and backscatter from the sample causes the frequencies of the pulses to lockup when the frequency difference between the pulses is too small. The frequency difference between the counter-rotating pulses is varied and the dead zone is detected. Backscatter from the sample is determined from the detected dead zone.

Additional objects, advantages, and novel features of the invention will become apparent to those skilled in the art upon examination of the following description or may be learned by practice of the invention. The objects and advantages of the invention may be realized and attained as particularly pointed out in the appended claims.

BRIEF DESCRIPTION OF THE DRAWINGS

The accompanying drawings, which are incorporated in and form part of the specification, illustrate an embodiment of the present invention and, together with the description, serve to explain the principals of the invention.

DETAILED DESCRIPTION OF THE INVENTION

This invention utilizes a short pulse ring laser modified such that the sample under test is located where the pulses overlap. In this configuration, backscatter caused by the sample is measurable as a change in beat frequency of the ring laser gyro.

Figure 1:
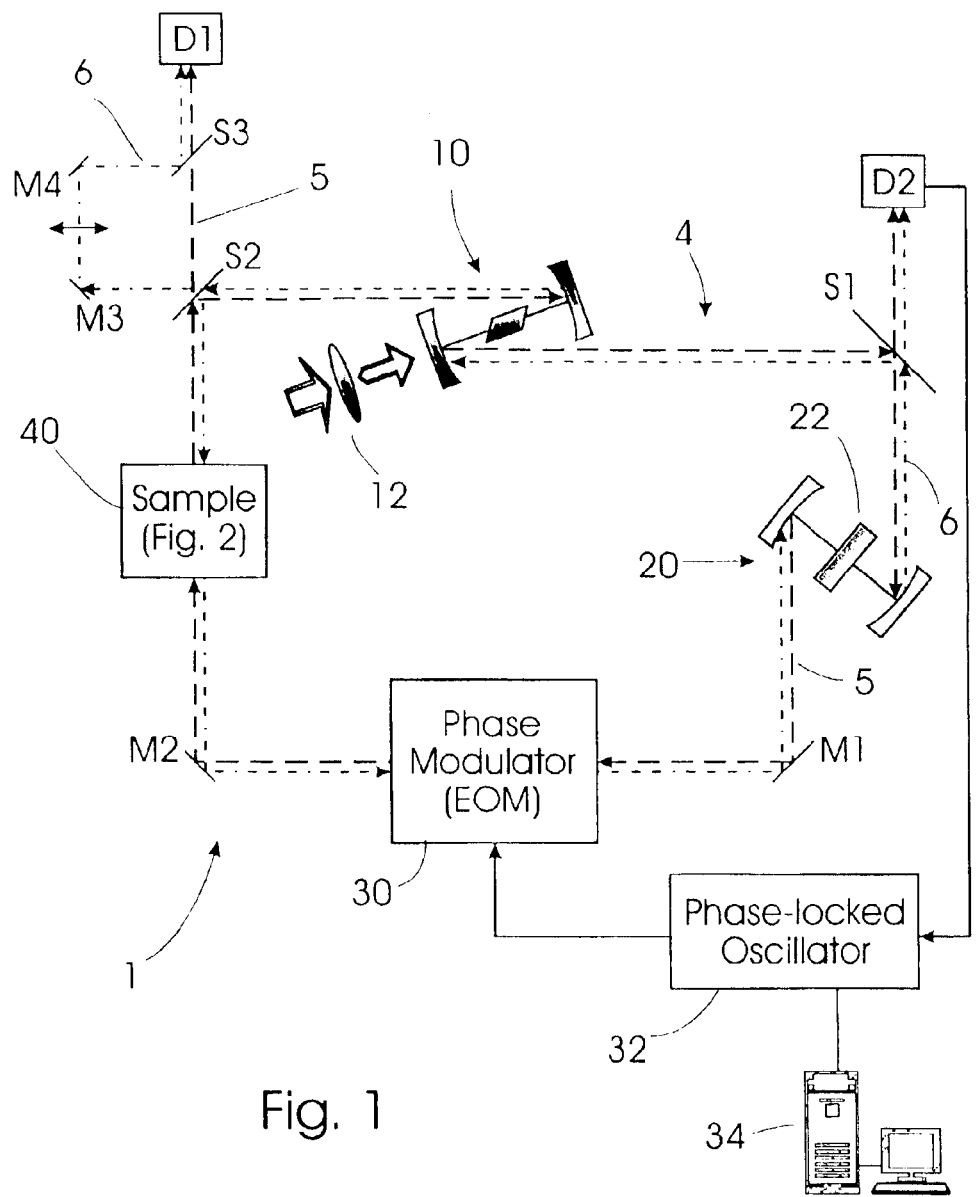
FIG. 1 shows a schematic diagram of an embodiment of the invention.

FIG. 1 shows scatterometer 1 according to an embodiment of the invention to include a relatively conventional ring laser cavity. To simplify the understanding of the present invention, the ring laser cavity is represented as containing four relatively equally spaced elements around an optical path 4. For the relatively square optical path 4 of FIG. 1, M1–M4 represent mirrors that reflect an entire beam and S1–S3 represent optical beam splitters that reflect a portion of a beam and pass the remainder of the beam. The paths of the two counter-rotating pulse trains that are common to an RLG are illustrated as paths 5, 6 that are slightly spaced and with different formats in FIG. 1. It should be understood that pulse paths 5, 6 actually overlap and follow the one optical path 4 of the scatterometer 1. Hereinafter, path or pulse 5 will refer to pulses moving clockwise in the RLG of FIG. 1, and path or pulse 6 will refer to pulses moving counterclockwise.

Details of the construction of a ring laser are set forth in the aforementioned book, *Ultrashort Laser Pulse Phenomena*, which details are incorporated herein by reference.

The optical path 4 in a test embodiment had a length of about one meter. As will be seen hereinafter, the position of some elements along optical path 4 is critical, as counter-rotating pulses must either overlap or not overlap at certain elements. One of ordinary skill will recognize that many path mediums, shapes, and lengths may be employed in the implementation of the optical path.

A CW laser such as an Argon laser 12 pumps a Ti:sapphire crystal to input energy and provide gain 10 for the ring laser. Examples of other gain elements which may be utilized are LiSAF, Eurbium doped glass, YAG and Alexandrite crystals. Gain 10 generates energy in both directions around optical path 4.

As is known in the art, pulse generation in a ring laser begins with noise that evolves into a train of pulses. Pulse generation occurs because of mode locking that is induced by prisms or quantum well devices (not shown) that are placed in the optical path in a manner well known to those of ordinary skill in the art. The counter-propagating pulses cross at a saturable absorber 20 that shortens the pulses traversing the optical path in a manner well known in the art. A dye jet absorber 20 was used in the test embodiment, although a movable multiple quantum well absorber or any other absorber or equivalent device which performs pulse shortening on the crossing pulses, yet avoids lock-up between the pulses, is contemplated in the practice of the invention.

An electro optical modulator (EOM) 30, as discussed above and in the '230 patent, is spaced from absorber 20 at a location along the optical path 4 where the counter-rotating pulses 5, 6 do not overlap. A phase-locked oscillator 32 applies a varying voltage to EOM 30 to control the optical path length inside the cavity independently for pulses 5, 6. Electrical inputs to the oscillator 32 include a voltage from detector $D_2$ as discussed hereinafter. A computer-controlled sweep voltage 40 may also be applied to oscillator 32 in order to provide the output of FIG. 3, as discussed below.

A beat note detector $D_1$ measures the difference in phase velocity between the two pulses and identifies the dead band. Such detectors are common in this art. Detector $D_1$ preferably receives both pulses at the same time; however, the only two places in the optical path where pulses 5, 6 cross are saturable absorber 20 and sample 40. As shown in FIG. 1, clockwise pulse 5 travels a longer distance from saturable absorber 20 to splitter S2 than does counterclockwise pulse 6. By making pulse 6 travel an extra loop S2, M3, M4, S3 equal to the difference in path lengths, the two pulses arrive simultaneously at detector $D_1$, The length of the loop is adjustable, as indicated by the arrow between M3 and M4.

Figures 2A, 2B:
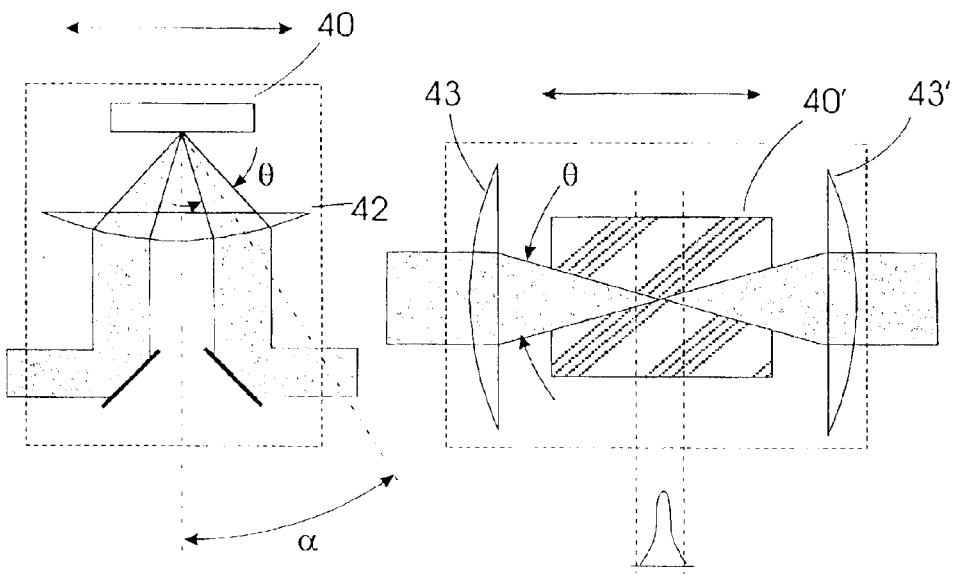
FIGS. 2A and 2B show, respectively, reflecting and transmitting samples under test in the invention.

Sample 40 is an element of this invention that is not common to prior art ring lasers, as it is in optical path 5 at a location where the pulses cross. Prior art ring lasers treat backscatter from any surface as undesirable; this invention utilizes the dead zone created by backscatter from sample 40 as a measurement of the surface properties of the sample. The position of sample 40 in the optical path is equidistant along each of paths 5, 6 from absorber 20, which is also a pulse crossing point. Sample 40 may be mounted on a translation stage for movement, as indicated in FIGS. 2A, 2B, to either position the pulse crossing point with respect to the incidence point of the beam on the sample for measurements, or to move the sample off the crossing point in order to monitor the operation of the ring laser.

Since scatterometer 1 does not physically rotate, counter-rotating pulses 5, 6 would be at almost identical frequencies that differ as a result of rotation of the earth). In order to record the dead zone during measurement of a sample, artificial rotation of scatterometer 1 is produced with EOM 30. Detector $D_2$ senses the rotating pulse trains and synchronizes oscillator 32. One circulating pulse (5 or 6) traverses the EOM 30 at the peak of the signal from oscillator 32, and therefore sees a different index of refraction than the pulse circulating in the opposite direction (6 or 5). The frequency of each pulse train is a function of the effective length of the optical path, and the effective length is a function of the index of refraction.

A periodic signal or "beat" is observed on detector D1 if the two beams have slightly different wavelength. There is a lowest (minimum) frequency that can be observed if any coupling (by scattering) is introduced at an intracavity crossing point of the two pulses. The physical reason for this "dead zone" (region of zero beat note) is that the scatterer (sample 40) injects a fraction $r^2$ of the clockwise circulating laser intensity into the counter-clockwise cavity, thereby "locking" the two frequencies (or wavelengths) together. The minimum frequency beat that can be observed is equal to half the field scattering coefficient r divided by the cavity round-trip time (typically 10 ns), or $$r = \pi \Delta f_{lock} \tau_{RT} \qquad \text{eq. 2.}$$

The beat note has been measured over a range of 1 Hz to 40 MHz in a system generating pulses of 30 fs (3E-13 seconds) duration.

Samples can be studied either in reflection or in transmission. A typical arrangement as sketched in FIG. 2A measures reflective backscattering in a fixed geometry. The solid angle θ under which the backscattering from sample 40 is being measured is mainly determined by the power of the lens 42. The separation between the two beams incident on the lens determines the angle of observation α. It should be noted that the scattering of the lenses and/or reflecting optics does not affect the measurement, as long as the pulse length is short compared to the distance lens-sample. Pulse length in the disclosed embodiment is on the order of 100 nm.

As shown in FIG. 2B, two lenses or parabolic reflectors 43, 43' can be used to focus the intracavity beam within a transmissive sample 40'. Direct backscattering is measured within a solid angle θ, again mainly determined by the power of the lens. The scattering volume can be calculated from the beam cross-section and the pulse length (the speed of light times the pulse duration). In order to prevent surface effects, the sample length should be large compared to pulse length, which is 30 $\mu$m for a 100 fs pulse.

The minimum measured scattering (not yet minimum BRDF) corresponds to a lock-in dead band equal to the beat note bandwidth. Referring to a typical measured response of a Ti:Sapphire ring laser, the bias (frequency difference between the pulses) of 325 Hz can be compensated by adjusting the phase modulator 30 shown in FIG. 1. Taking the minimum measurable lock-in frequency to be the 3 Hz bandwidth of the beat note, equation 2 shows a sensitivity to a field reflection coefficient of $r=10^{-7}$ or an intensity reflection of $10^{-14}$. Choosing the lenses in FIG. 2 to produce an f=8.85 light cone to strike the surface of the mirror under test, the resulting solid angle will be 0.01 sr and the minimum detectable BRDF will be $10^{-12}$/sr. A bit more challenging but still possible, would be an f=2.8 light cone giving a solid angle of 0.1 sr for a detection threshold of $10^{-13}$/sr, which compares favorably with current capability of BRDF measurements ranging from $10^{-6}$ to $10^{-7}$/sr.

Figures 3A, 3B:
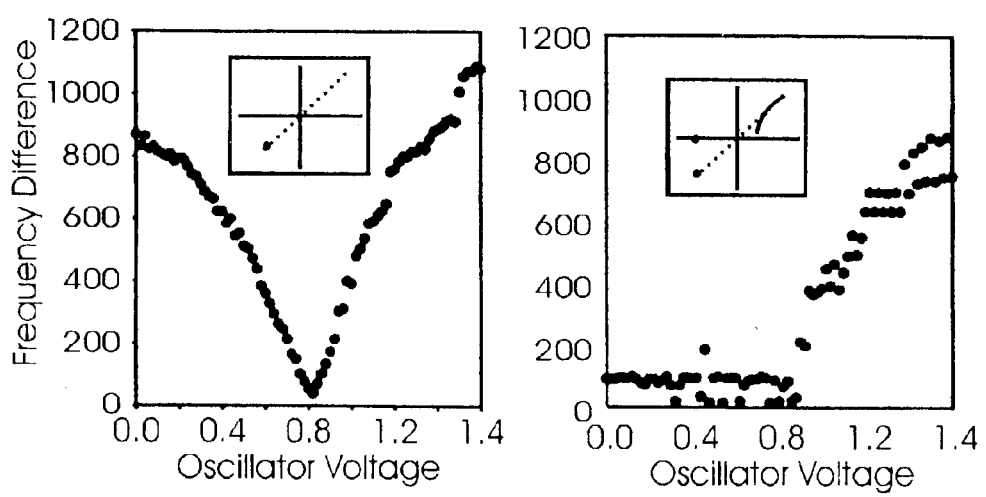
FIGS. 3A and 3B show, respectively, the detected output for transmitting samples without and with backscatter.

FIG. 3 shows the dependence of the beat note on the voltage applied to the electro-optic modulator. In FIG. 3A, curve is recorded in the absence of the sample 40' at the second crossing point. Since, for this curve, there is no structure in the optical path at the pulse crossing point, the vertical axis shows the beat frequency goes to lock-up only when the voltage applied to oscillator 34 adjusts the frequency of one pulse to be equal to the frequency of the other pulse. FIG. 3B shows the same measurement with an antireflection-coated BK7 plate as a sample 40'. The frequency was calculated using a chirp z transform from the data collected by an acquisition card as the voltage was changing. The insert inside each of FIGS. 3A, 3B is a visual reminder of equation 1 where the beat note is proportional to the applied voltage in the EOM due to the change in the refractive index. Without the sample, a residual beat note of approximately 900 Hz is present. With a proper phase adjustment, using the EOM, it is possible to overcome that phase velocity difference in a way that an increase in the voltage in the modulator will decrease the beat note and eventually bring it to zero. Beyond that point, any increase in the voltage in the modulator will generate a gradual increase in the beat note.

The presence of a transmissive BK7 plate with an antireflection coating as scatterer 40 changes the response of the beat note, and a dead band is clearly identified in FIG. 3B. In this case, a large enough bias in the modulator is needed to overcome the injection locking from one direction to the other in the cavity due to the scatterer, the low bias in the modulator being insufficient to produce the beat note, an indication of a dead band. A clear oscillation is produced only with high modulation bias.

For this preliminary work, the beat note threshold below which the pulses lock is around 200 Hz, which corresponds to an intensity backscattering coefficient of $R=3.6\times10^{-11}$. These results show that by controlling the change in the refractive index as a nonreciprocal media and using the lock up of the beat note in a bidirectional pulsed ring laser, it is possible to measure very small scattering amplitudes.

One of ordinary skill in the art will recognize that many of the elements of this invention may be implemented with equivalents to the elements disclosed herein. For example, gain elements other than Ti:sapphire may also be used. A number of pump sources may be used in the invention. The physical layout is described herein as a square to aid in the understanding of the invention; any optical path that maintains the relationships between elements and crossing points disclosed herein may be utilized. And while a pulse frequency is disclosed with only two circulating pulses, a higher pulse rate could be utilized so long as pulses only cross at the sample and non-scattering surfaces such as the absorber. It is intended that this invention is defined by the scope of its claims.

What is claimed is:

1. A scatterometer comprising:
    a ring laser for generating counter-rotating pulses within a continuous optical path, said pulses having a pulse length much less than the length of said optical path;
    a sample located in said optical path at a location where the counter-rotating pulses cross;
    means for varying a frequency difference between said counter-rotating pulses; and
    a detector of the frequency difference between said counter-rotating pulses, said detector detecting a dead zone when the frequency difference between the pulses is too small and backscatter from the sample causes the counter-rotating pulses to lock-up, wherein backscatter from said sample is a function of the width of the detected dead zone.

2. The scatterometer of claim 1 wherein said ring laser includes an absorber for shortening said pulses, said pulses not locking-up at said absorber, wherein said absorber and said sample are the only two physical parts in said optical path where said pulses cross.

3. The scatterometer of claim 2 wherein said means for varying the frequency difference comprises a modulator in said optical path for controllably changing the frequency of one of said pulses with respect to said other pulse.

4. The scatterometer of claim 3 wherein said modulator comprises an electro-optical modulator, said modulator changing its index of refraction in response to a control signal activated by the passage of one of said pulses.

5. The scatterometer of claim 4 further comprising a detector responsive to only one of said pulses, the control signal being an output from said detector.

6. The scatterometer of claim 5 further comprising a voltage-controlled oscillator driving said electro-optical modulator, said detector output controlling the frequency of said oscillator.

7. The scatterometer of claim 6 further comprising a computer controllably sweeping said beat frequency across the dead zone.

8. The scatterometer of claim 1 wherein said sample is mounted on a fixture, said fixture being moveable along said optical path to position said sample at the location where said pulses cross.

9. The scatterometer of claim 8 wherein said sample is transmissive.

10. The scatterometer of claim 8 wherein said sample is reflective.

11. A method of measuring backscattering from an optical sample comprising:

generating counter-rotating pulses along a continuous optical path of a ring laser, the pulses having a pulse length much less than the length of said optical path;

varying a frequency difference between said counter-rotating pulses;

placing the sample in the optical path at a location where the counter-rotating pulses cross, wherein backscatter from the sample causes the frequencies of the pulses to lockup when the frequency difference between the pulses is too small;

detecting a dead zone where the frequencies are locked up; and determining backscatter of the sample from said detected dead zone.

12. The method of claim 11 wherein the only physical structure in said ring laser at any location where said pulses cross are the sample and an absorber, the pulses not locking up at the absorber.

13. The method of claim 12 wherein said scatterometer further comprises a modulator in said ring laser optical path, and said step of varying a frequency difference comprises varying the index of refraction in said modulator when one pulse is passing relative to the index of refraction in said modulator when said other pulse is passing.

14. The method of claim 13 further comprising:

detecting one pulse at said modulator; and applying a control signal to said modulator when said one pulse is detected, said control signal controlling the index of refraction in said modulator.

15. The method of claim 11 further comprising sweeping said frequency difference across the dead zone caused by said sample.

* * * * *